United States Patent
Todd et al.

(10) Patent No.: US 10,139,291 B2
(45) Date of Patent: Nov. 27, 2018

(54) SENSOR CALIBRATION METHOD AND APPARATUS

(71) Applicant: Sphere Medical Limited, Cambridge, Cambridgeshire (GB)

(72) Inventors: Neil Todd, Cambridge (GB); Steven Fowler, Cambridge (GB); Gavin Lucius Troughton, Cambridge (GB)

(73) Assignee: Sphere Medical Limited (GB)

( * ) Notice: Subject to any disclaimer, the term of this patent is extended or adjusted under 35 U.S.C. 154(b) by 435 days.

(21) Appl. No.: 14/782,877

(22) PCT Filed: Apr. 7, 2014

(86) PCT No.: PCT/GB2014/051077
§ 371 (c)(1),
(2) Date: Oct. 7, 2015

(87) PCT Pub. No.: WO2014/167303
PCT Pub. Date: Oct. 16, 2014

(65) Prior Publication Data
US 2016/0033340 A1 Feb. 4, 2016

(30) Foreign Application Priority Data

Apr. 8, 2013 (GB) .................................. 1306321.9

(51) Int. Cl.
*G01K 15/00* (2006.01)
*A61B 5/1495* (2006.01)
*A61B 5/145* (2006.01)

(52) U.S. Cl.
CPC .......... *G01K 15/005* (2013.01); *A61B 5/1495* (2013.01); *A61B 5/145* (2013.01);
(Continued)

(58) Field of Classification Search
CPC .......... G01N 33/5438; G01N 27/3274; G01N 33/66; G01N 33/5302; G01N 21/3577;
(Continued)

(56) References Cited

U.S. PATENT DOCUMENTS 4,941,308 A * 7/1990 Grabenkort ......... A61M 25/002
53/425
5,329,804 A * 7/1994 Germany ............. A61B 5/1491
73/1.06
(Continued)

FOREIGN PATENT DOCUMENTS

GB  2457660 A  8/2009
WO  2004/040284 A1  5/2004
(Continued)

OTHER PUBLICATIONS

International Search Report for corresponding application No. PCT/GB2014/051077.
(Continued)

*Primary Examiner* — Gail Kaplan Verbitsky
(74) *Attorney, Agent, or Firm* — Wood, Phillips, Katz, Clark & Mortimer

(57) ABSTRACT

Disclosed is a method for calibrating a sensor of a monitoring apparatus for monitoring an analyte concentration in a body fluid sample of a patient in which a temperature-dependent drift model is derived for the sensor. An apparatus for monitoring an analyte concentration in a body fluid sample of a patient including such a sensor and a signal processor programmed to calibrate the sensor in accordance with this method is also disclosed.

12 Claims, 5 Drawing Sheets

Figure 1:
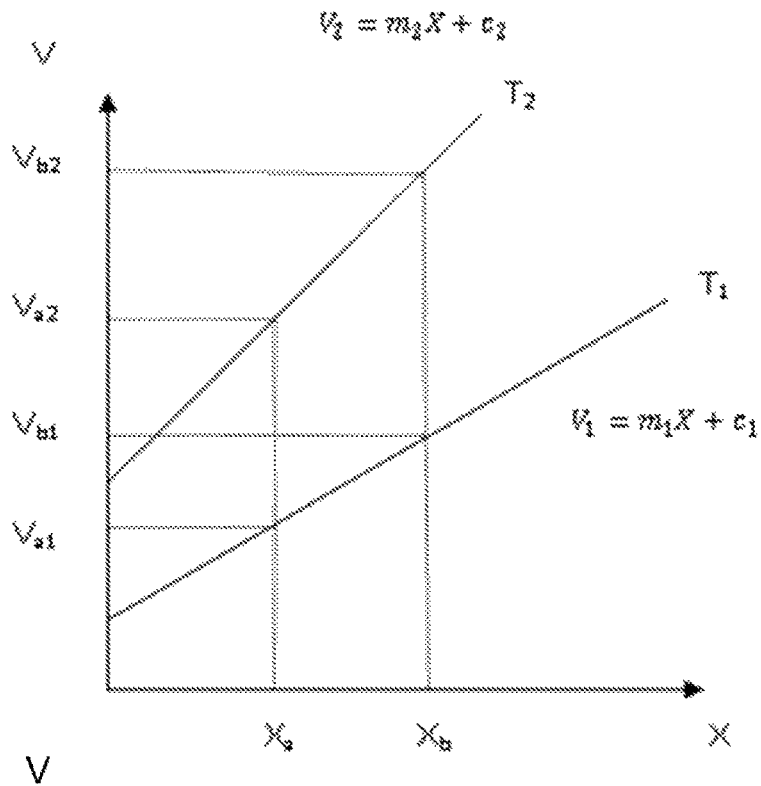

(52) U.S. Cl.
CPC ... *A61B 5/14542* (2013.01); *A61B 2560/0223* (2013.01); *A61B 2560/0228* (2013.01)

(58) Field of Classification Search
CPC .......... C12Q 1/54; C12Q 1/001; C12Q 1/006; G01K 15/005; A61B 2560/0223; A61B 2560/0228; A61B 5/145; A61B 5/14542; A61B 5/1495; A61B 5/14546; A61M 2230/201
See application file for complete search history.

(56) References Cited

U.S. PATENT DOCUMENTS

| | | | |
|---|---|---|---|
| 5,763,760 A * | 6/1998 | Gumbrecht | A61B 5/14539 73/1.06 |
| 6,620,121 B1 * | 9/2003 | McCotter | F04B 43/08 422/44 |
| 7,951,069 B2 * | 5/2011 | Bertolero | A61B 1/12 600/114 |
| 8,607,612 B2 * | 12/2013 | Barwell | G01N 33/5438 374/1 |
| 8,746,031 B2 * | 6/2014 | Crane | A61B 5/14532 73/1.03 |
| 8,869,585 B2 * | 10/2014 | Troughton | A61B 5/1495 73/1.03 |
| 2009/0018426 A1 | 1/2009 | Markle et al. | |
| 2009/0030641 A1 * | 1/2009 | Fjield | A61B 5/14532 702/104 |
| 2009/0177406 A1 | 7/2009 | Wu | |
| 2011/0224516 A1 | 9/2011 | Romey | |
| 2012/0215460 A1 | 8/2012 | Wu et al. | |
| 2012/0240656 A1 * | 9/2012 | Crane | A61B 5/14546 73/1.03 |
| 2012/0262298 A1 | 10/2012 | Bohm | |
| 2013/0083820 A1 * | 4/2013 | Barwell | G01N 33/5438 374/1 |
| 2015/0074575 A1 * | 3/2015 | Jeon | G06F 3/04886 715/768 |
| 2015/0090589 A1 * | 4/2015 | Estes | A61B 5/14865 204/403.1 |
| 2016/0033341 A1 * | 2/2016 | Tadigadapa | G01K 7/32 374/31 |

FOREIGN PATENT DOCUMENTS

| | | | |
|---|---|---|---|
| WO | WO 2008141243 A2 * | 11/2008 | ......... A61B 5/14532 |
| WO | 2012/164268 A1 | 12/2012 | |
| WO | 2013/072669 A1 | 5/2013 | |

OTHER PUBLICATIONS

Search Report for corresponding UK Application No. GB1306321.9 dated Oct. 11, 2013.

Examination Report for UK Application No. GB1306321.9 dated Jan. 31, 2018.

* cited by examiner

SENSOR CALIBRATION METHOD AND APPARATUS

FIELD OF THE INVENTION

The present invention relates to a method of calibrating a sensor of an apparatus for monitoring an analyte concentration in a body fluid sample of a patient.

The present invention relates to a method of calibrating a sensor of an apparatus for monitoring an analyte concentration in a bodily fluid sample of a patient.

BACKGROUND OF THE INVENTION

Certain methods of medical treatment of patients may require the monitoring of one or more analyte concentrations in bodily fluids, including gasses such as oxygen ($O_2$) and carbon dioxide ($CO_2$), electrolytes including sodium ($Na^+$) and potassium ($K^+$), metabolites including glucose and biomolecules such as proteins. In addition, such analytes may comprise entities suspended in the fluid, e.g. the concentration of red blood cells, as expressed by a parameter called haematocrit.

To facilitate such monitoring, the patient may be connected to a monitoring system which incorporates one or more sensor(s) for the detection of the analytes described above. This arrangement has a distinct advantage over a regime where patient samples are drawn intermittently and sampled on a standalone device such as a blood gas analyser. First, as the sensor is constantly exposed to the patient sample, changes in analyte levels are monitored in real-time. This enables the clinician to view trends in analyte concentration changes and to respond more quickly to critical changes. This reduces the risk that potential complications in the medical treatment of the patient are detected late.

In addition, this method is less susceptible to artefacts that may arise from drawing the sample from the patients and transporting it to the stand alone measuring device. Therefore, continuous monitoring reduces the risk of inappropriate clinical decisions being made based on inaccurate measurements arising due to sample handling errors. For example, $CO_2$ and $O_2$ levels in the blood can change in a sampling syringe with time, giving rise to inaccurate reading of the extracted patient sample. In addition, red blood cell lysis due to these extra sample handling steps can lead to changes in the concentration of blood electrolytes, particularly $K^+$.

Many different types of sensor are known. For example, WO99/17107 discloses a glucose sensor for continuous monitoring. Many other examples are known to those who are skilled in the art.

In order for a sensor to monitor an accurate reading, the output of the sensor must first be calibrated by exposing the sensor to one or more fluids which contain a known concentration of the analyte of interest. Using interpolation and knowledge of the response curve of the sensor signal versus analyte concentration, it is possible to construct a calibration curve of the signal versus analyte concentration over the required measurement range. This calibration curve can then be used to determine the concentration of analyte in a test sample from the measured response of the sensor when it is exposed to the same test sample. The concept of calibration is well known to those who are skilled in the art.

A fundamental property of a sensor is that the calibration coefficients determined during calibration often change with time and temperature. A change in the calibration coefficients with time is often referred to as sensor drift. For example, pH sensors based on Ion-Sensitive Field-Effect Transistor (ISFET) technology have a significant baseline (offset) drift and can show changes in both offset and sensitivity with changes in temperature as for instance is disclosed in "ISFET, Theory and Practice" by P. Bergveld in the Proc. IEEE Sensor Conference Toronto, October 2003, Pages 1-26. Amperometric oxygen sensors often show changes in sensitivity with time. Other drift characteristics of typical sensors are well known to those who are skilled in the art.

Several examples of drift correction and temperature dependence correction exist in the prior art. For example, in order to overcome the reduction in measurement accuracy due to sensor drift, the sensor can be periodically recalibrated by exposing it to one or more solution(s) with known analyte concentrations. The new calibration coefficients can then be applied to remove the contribution of sensor drift to the sensor reading. In addition, to compensate for the temperature dependence of the sensor readings, it is necessary to know the temperature that the calibration was performed at ($T_{cal}$) and the temperature of the sample being measured ($T_{sample}$). If the temperature dependence of the sensor is well characterised, it is possible to apply a transformation function $f(T_{cal}, T_{sample})$ for the sensitivity (a) and/or offset (b) respectively to remove the effect of the temperature change on the sensor response since the last calibration.

For sensors that exhibit a drift in temperature dependence with time, the situation is much more challenging. For these sensors, it is necessary to express the transformation function as a function of time $f(T_{cal}, T_{sample}, t)$. Obtaining an accurate model for this transformation is often extremely difficult, due to e.g. a variation in sensor characteristics from batch-to-batch.

For sensors with poorly characterised drift and/or temperature dependence, the problems described above are usually addressed by making intermittent readings of the patient sample on a second, standalone analyser. The analyte level measurement from this second analyser can then be compared with the reading from the sensor in the continuous monitoring system at the time the sample was taken. Any differences between these readings are attributed to sensor drift and the calibration coefficients can be adjusted to ensure the concentration measured by the continuous monitoring system at the time of sampling and the concentration measured by the second analyser are the same.

This process is known in the prior art as realignment. This realignment method has several significant drawbacks. First, the need to withdraw a sample from the system for analysis creates the potential for sample handling errors, e.g. gas levels in the sample may change in the interval between sampling and measurement. In addition, due to limitations on the sample volume that can be drawn from a patient, the frequency of realignment is limited. This can compromise the reliability of the measurement, as sensor drift between realignment is not accounted for. The realignment process is also time consuming and inconvenient for the user. Finally, the realignment process does not allow the temperature dependence of the sensor to be measured accurately, so significant changes in temperature after the realignment period can lead to errors in the measurement results.

SUMMARY OF THE INVENTION

The present invention seeks to provide an improved method of calibrating a sensor of a monitoring apparatus for monitoring an analyte concentration in a bodily fluid sample of a patient.

The present invention further seeks to provide an apparatus for more accurately monitoring an analyte concentration in a bodily fluid.

In accordance with an aspect of the present invention, there is provided a method of calibrating a sensor of a monitoring apparatus for monitoring an analyte concentration in a bodily fluid sample of a patient, the method comprising performing a first calibration cycle by measuring a first response of the sensor to exposure to a first calibration fluid having a first concentration of said analyte at a first temperature; measuring a second response of the sensor to exposure to a second calibration fluid having a second concentration of said analyte at a second temperature; determining a temperature dependence in the sensitivity of the sensor from the first and second response; performing a second calibration cycle by repeating the first calibration cycle after a time interval; deriving a temperature-dependent drift function for the sensor from a difference in the temperature dependence determined in the first and second calibration cycles respectively; and generating a calibration curve including said temperature-dependent drift function for said sensor.

By providing a calibration curve in which the effect of temperature on drift is included, a transformation function with improved accuracy can be provided, thus improving the accuracy of the sensor over a range of temperatures during a prolonged period of time.

It is not necessary for the first calibration fluid and the second calibration fluid to have different concentrations of the analyte of interest. Instead, the first concentration and the second concentration may be the same. Indeed, the first calibration fluid and the second calibration fluid may be the same.

In an embodiment, the first calibration cycle further comprises measuring a third response of the sensor to exposure to a third calibration fluid having a third concentration of said analyte at a third temperature; and wherein the step of determining a temperature dependence in the sensitivity of the sensor comprises determining said sensitivity from the first, second and third responses. This enables the determination of a temperature-dependent drift function for a sensor having non-linear temperature-dependent drift characteristics.

The method may further comprise measuring a further response of the sensor to exposure to a first portion of a bodily fluid sample at a measurement temperature, said bodily fluid sample comprising an unknown amount of said analyte; and estimating the amount of said analyte in said sample from said further response using said calibration curve to obtain an accurate estimate of the concentration of the analyte of interest in the bodily fluid sample of the patient.

In an embodiment, the method further comprises exposing a reference apparatus to a second portion of the bodily fluid sample; determining the amount of analyte in said sample with said reference apparatus; comparing the estimated amount with the determined amount; and creating an updated calibration curve by repeating the steps of performing the first and second calibration cycles, deriving the temperature drift function and generating the calibration curve in case a difference between the estimated amount and the determined amount exceeds a defined threshold. By periodically validating (and if necessary correcting) the temperature-dependent drift function in this manner, the accuracy of the sensor is further improved.

The method may further comprise repeating the steps of performing the first and second calibration cycles, deriving the temperature-dependent drift function and generating the calibration curve after a predefined period of time. This further improves the accuracy of the sensor, as variations in the temperature-dependent drift function will be discovered and corrected in this manner.

The method may further comprise periodically exposing said sensor to a bodily fluid sample of the patient; and repeating the steps of performing the first and second calibration cycles, deriving the temperature drift function and generating the calibration curve upon an uncharacteristic change in the sensor response during said periodic exposure. This further improves the accuracy of the sensor as any unusual reading of the sensor is immediately verified by recalibrating the sensor and updating the temperature-dependent drift function in the calibration curve.

The generation of the calibration curve may further include measuring an initial response of the sensor to exposure to a first initial calibration fluid at an initial temperature, said first initial calibration fluid having a first further concentration of said analyte; generating an initial calibration curve for said sensor from the initial response; after a time interval, measuring an further response of the sensor to exposure to a second initial calibration fluid at an initial temperature, said second initial calibration fluid having a second further concentration of said analyte; deriving an initial drift function for the sensor from the first response and the second response; and updating the initial calibration curve with said initial drift function; and wherein the step of generating a calibration curve including said temperature drift function comprises updating the updated initial calibration curve. This facilitates a more straightforward generation of the temperature-dependent drift function by adjustment of the initial drift function.

According to another aspect of the present invention, there is provided a computer program product comprising a computer-readable storage medium, said medium comprising computer program code for implementing the method according to an embodiment of the present invention when executed on a processor of an apparatus for monitoring an analyte concentration in a bodily fluid sample of a patient. The computer-readable storage medium may be any medium that can be accessed by a computer for the retrieval of digital data from said medium. Non-limiting examples of a computer-readable storage medium include a CD, DVD, flash memory card, a USB memory stick, a random access memory, a read-only memory, a computer hard disk, a storage area network, a network server, an Internet server and so on.

According to yet another embodiment of the present invention, there is provided an apparatus for monitoring an analyte concentration in a bodily fluid sample of a patient, the apparatus comprising a sample chamber for receiving said bodily fluid sample, said sample chamber comprising a sensor for determining said analyte concentration in said bodily fluid sample; a fluid line fluidly connected to the sample chamber for providing the sensor with a calibration fluid; a temperature control element for controlling the temperature of the calibration fluid in the sample chamber; the computer program product according to an embodiment of the present invention; and a signal processor conductively coupled to the sensor, said signal processor being adapted to execute the computer program code of said computer program product. This apparatus benefits from having a sensor that can be read out with an improved accuracy due to the fact that the signal processor interprets the sensor signals using the calibration curve including the temperature-dependent drift function.

Advantageously, the signal processor is further adapted to control the temperature control element in a calibration mode of said sensor.

The temperature control element may be placed in the sample chamber to improve the control over the temperature of a sample in the sample chamber.

The apparatus may further comprise a temperature sensor for monitoring the temperature of a sample in the sample chamber to further improve the accuracy of the sensor, as any sensor reading can be correlated to the measured temperature.

In an embodiment, the apparatus is a cardiopulmonary bypass apparatus.

BRIEF DESCRIPTION OF THE EMBODIMENTS

Figure 2:
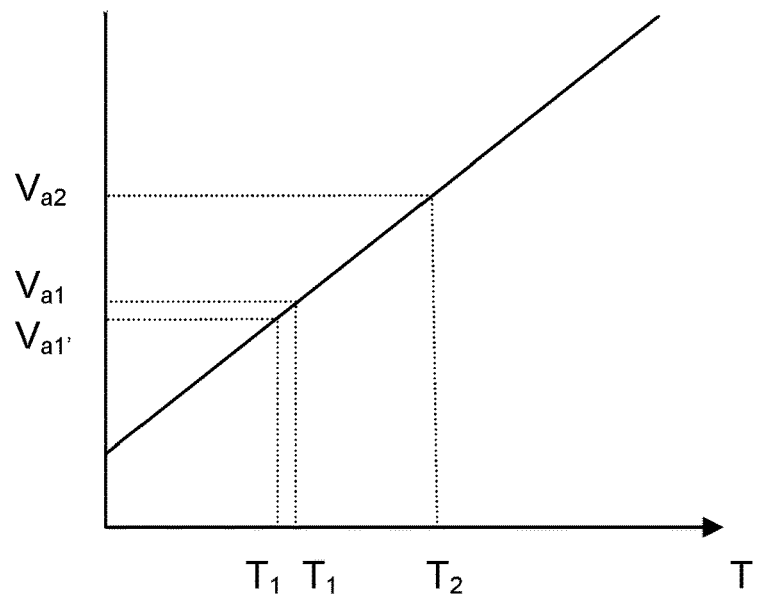
Figure 3:
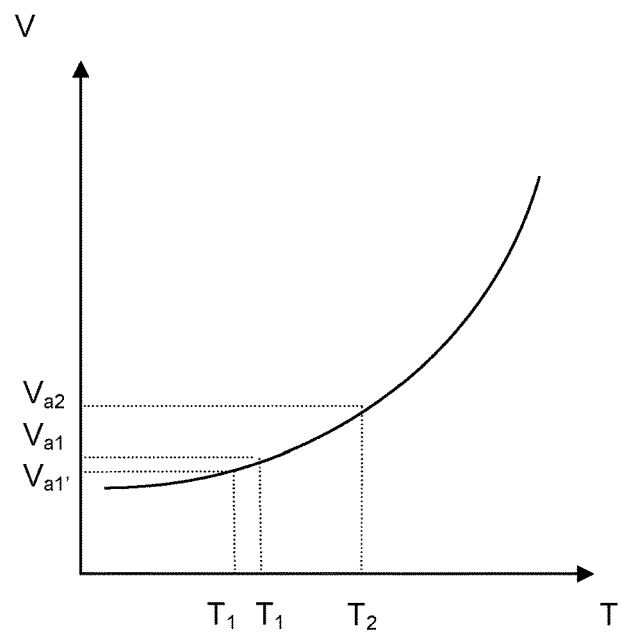
Figure 4:
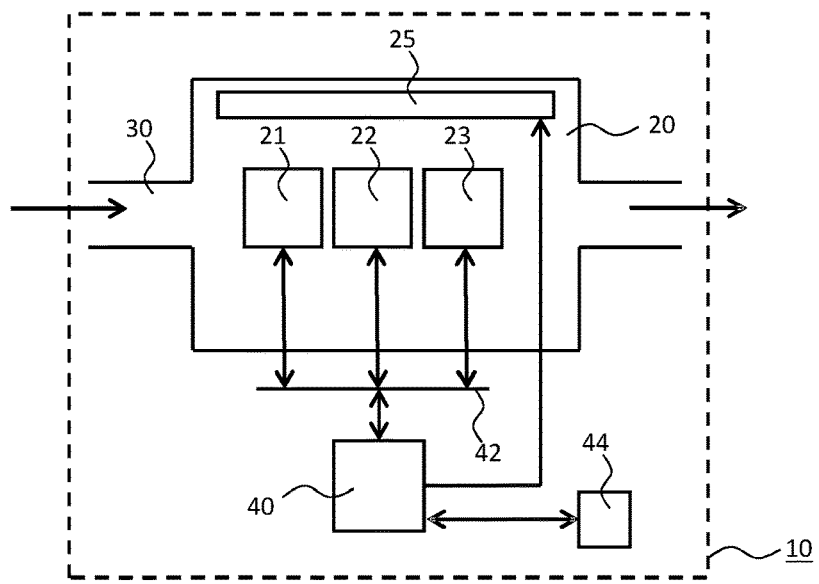
Figure 5:
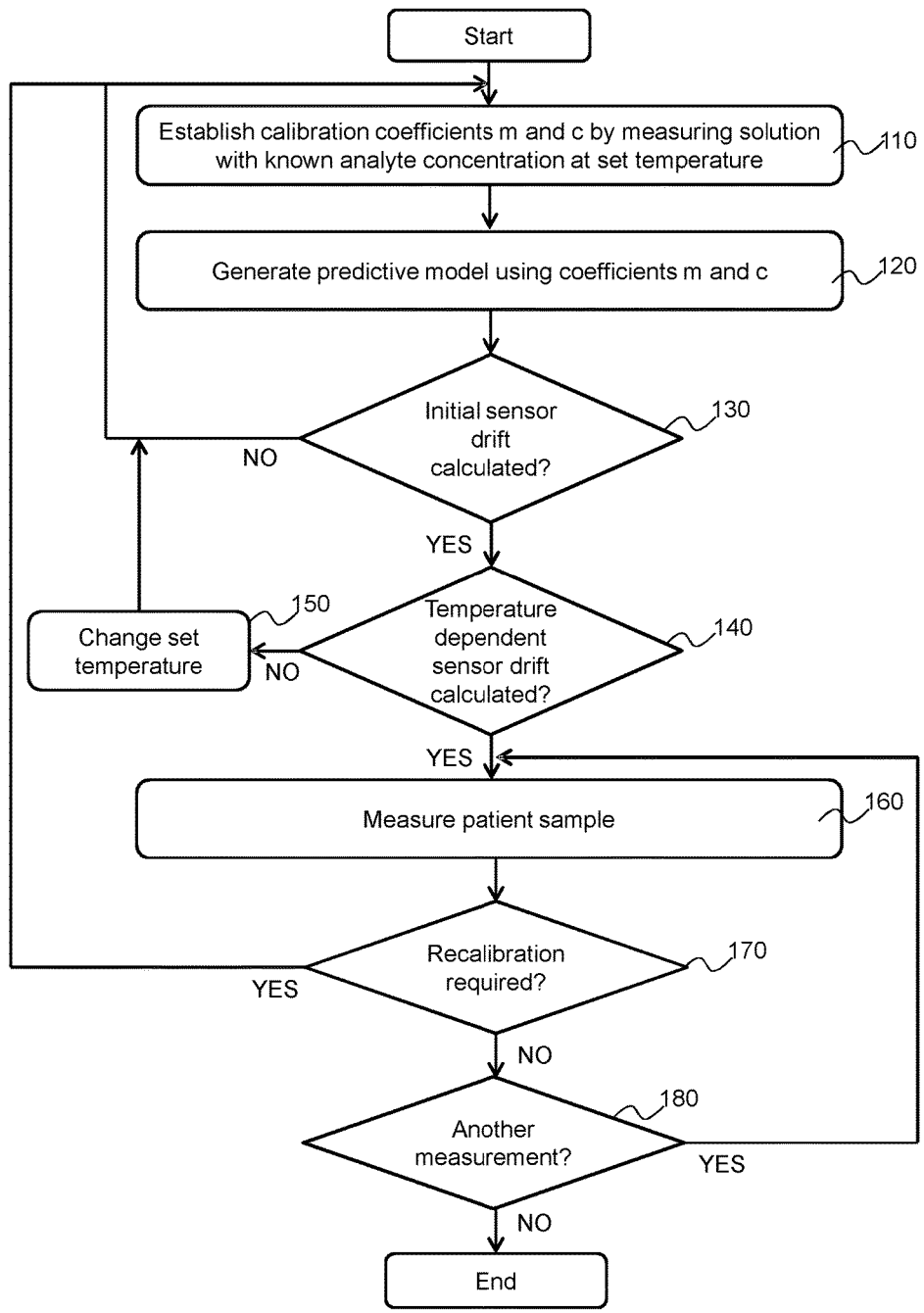
Figure 6:
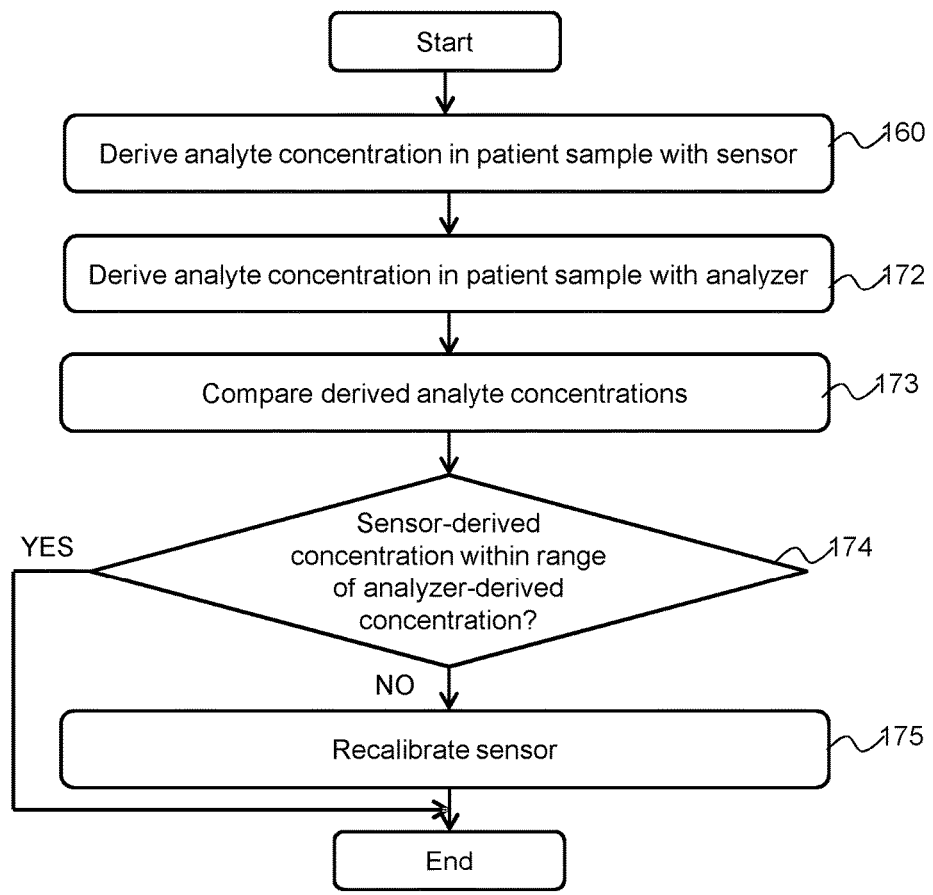
Figure 7:
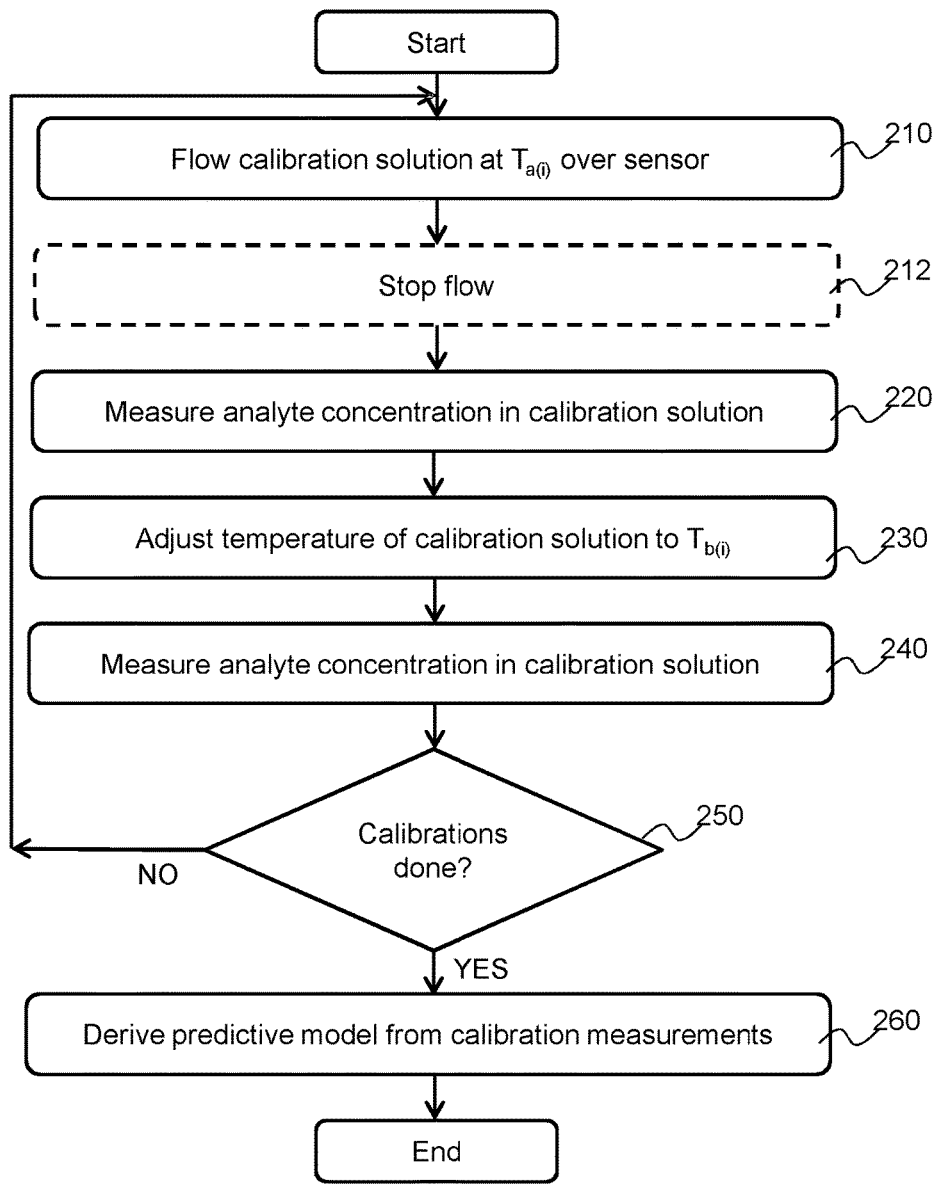

Embodiments of the invention are described in more detail and by way of non-limiting examples with reference to the accompanying drawings, wherein:

FIG. 1 schematically depicts a response characteristic of a sensor;

FIG. 2 schematically depicts another response characteristic of a sensor;

FIG. 3 schematically depicts yet another response characteristic of a sensor;

FIG. 4 schematically depicts an embodiment of an apparatus of the present invention;

FIG. 5 schematically depicts a flow chart of a method according to an embodiment of the present invention;

FIG. 6 schematically depicts a flow chart of an aspect of a method according to an embodiment of the present invention; and FIG. 7 schematically depicts another aspect of a method according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

Generally, a sensor such as a sensor in an apparatus for monitoring an analyte in a bodily fluid of a patient requires calibration such that the signal produced by the sensor can be correlated to an analyte concentration in a sample to which the sensor is exposed.

For instance, where a sensor has an output signal V that has a linear dependence on analyte concentration (X), the relationship can be described in the form V=mX+c, where m is the sensitivity and c is the offset, as shown in FIG. 1. Where the offset is non-zero, two calibration solutions of different analyte level ($X_a$ and $X_b$) are needed to characterise the sensor.

The sensor signal V in FIG. 1 is also temperature-dependent. In this case, there are two possibilities. The first possibility is that the sensor is operated at a single temperature only, in which case this temperature dependence can be ignored. The second possibility is that the sensor is expected to operate over a temperature range, in which case the temperature dependence must also be characterised. For two temperatures, $T_1$ and $T_2$, the sensor signal as a function of analyte concentration can be represented by $V_1=m_1X+c_1$ at $T_1$ and by $V_2=m_2X+c_2$ at $T_2$.

The sensor signal at a measurement temperature T can be expressed as $V_T=m_TX+c_T$. Where the sensor signal has a linear dependence on temperature as shown in FIG. 2, it can be shown that:

$$m_T = \left(\frac{T-T_1}{T_2-T_1}\right)(m_2 - m_1) + m_1 \quad (1)$$

$$c_T = \left(\frac{T-T_1}{T_2-T_1}\right)(c_2 - c_1) + c_1 \quad (2)$$

such that an accurate estimate of the analyte concentration at the measurement temperature T can be derived from signal $V_T$ using the above equations (1) and (2).

In the more difficult case of a non-linear dependence on temperature as shown in FIG. 3, measurements must be made at at least three temperatures and non-linear regression and a more complex model must be used to derive the calibration at a given temperature. Alternatively, using prior knowledge of the non-linear dependence, an approximate fit can be made using calibration at two temperatures, which may reduce the error obtained over that resulting if a linear model is used.

The thus obtained calibration coefficients m and c have a limited validity, as various effects such as sensor ageing and fouling will cause these coefficients to change or drift over time, such that over time the accuracy of the sensor readings can deteriorate. This may be addressed by periodic recalibration of the sensor to provide updated sensor coefficients, thus maintaining the accuracy of the sensor readings over time. This however is not ideal in a situation where the monitoring apparatus should provide constant monitoring of a patient, as the periodic calibration cycles disrupt the monitoring function of the apparatus. A cardiopulmonary bypass machine is a non-limiting example of such an apparatus. Other examples for instance include in-line blood monitors.

To reduce the calibration frequency of such an apparatus, the calibration coefficients may include a prediction of the sensor drift behaviour, as for instance is disclosed in WO2009/104016 A2, which discloses that initially obtained calibration coefficients may be periodically updated using a calculated sensor drift. However, such approaches fail when the drift itself is also temperature-dependent.

The present invention seeks to improve the reliability of sensor drift calculations for use in the calibration curve of a sensor such that the required recalibration frequency can be further reduced, thus increasing the period of continuous use of the apparatus including the sensor.

FIG. 4 schematically depicts an apparatus 10 for monitoring an analyte concentration in a bodily fluid sample of a patient according to an embodiment of the present invention. The apparatus 10 comprises a sample chamber 20 in which a number of sensors are located. Three sensors 21-23 are shown by way of non-limiting example only; it should be understood that the sample chamber 20 may comprise any suitable number of sensors, e.g. one or more sensors.

The sample chamber 20 is fluidly connected to a flow path or fluid line 30 for supplying a sample or calibration fluid to the sample chamber 20. Preferably, the apparatus 10 is arranged to perform calibration or sample measurements whilst the fluid is flowing over the one or more sensors 21-23 although the present invention is not limited thereto; instead, the apparatus 10 may be arranged to perform calibration or sample measurements whilst the fluid is stationary over the one or more sensors 21-23.

The apparatus 10 further comprises a temperature control stage 25 for controlling the temperature of a fluid in the sample chamber 20. In an embodiment, the temperature control stage 25 is located inside the sample chamber 20 although it should be understood that other arrangements, e.g. placement of the temperature control stage 25 in the fluid line 30 or in any other location from where the temperature of the fluid in the sample chamber 20 may be controlled. In an embodiment, the temperature control stage 25 comprises a heating element. In yet another embodiment, the temperature control stage 25 is thermally coupled to at least one of the sensors 21-23 to control the temperature of the at least one sensor. The temperature control stage 25 may for instance be integrated in the at least one sensor or placed in the vicinity of the at least one sensor.

The apparatus further comprises a signal processor 40 for processing the signals of the sensors 21-23 and for controlling the temperature control stage 25. By way of non-limiting example, the signal processor 40 is communicatively coupled to the sensors 21-23 via a data communication bus 42, although it should be understood that one or more of the sensors 21-23 may be coupled to the signal processor 40 via dedicated wiring, e.g. conductive tracks of a printer circuit board. In an embodiment, one of the sensors 21-23 may be a temperature sensor for determining the temperature in the sample chamber 20 and/or for determining the temperature of the sensor(s) to be calibrated. Such a temperature sensor is typically conductively coupled to the signal processor 40 to allows the signal processor 40 to process the measured temperature, e.g. in a temperature-dependent calibration process of one or more sensors to be calibrated.

The apparatus 10 further comprises a data storage medium 44 that can be accessed by the signal processor 40 such as a RAM memory, ROM memory, solid state memory, hard disk and so on. The data storage medium 44 comprises program code that can be executed by the signal processor 40 to configure the signal processor 40 to implement an embodiment of the method of the present invention, which will be discussed in more detail below. In accordance with embodiments of the method of the present invention, the signal processor 40 is configured to generate a calibration curve for at least one of the sensors 21-23 in which sensor drift as a function of temperature is included in the calibration curve such that the signal of a thus calibrated sensor can be accurately correlated to a concentration of the analyte to which the sensor is sensitive over a prolonged period of time, thus reducing the required recalibration frequency.

FIG. 5 shows a flowchart of a calibration method according to an embodiment of the present invention. The method starts by progressing to step 110 at point in time $t=t_1$, in which a first calibration fluid having a first concentration $X_1$ of the analyte of interest and a temperature $T_1$ is passed through the sample chamber 20 and a sensor signal of the sensor to be calibrated that is generated by the exposure of the sensor to the first calibration fluid is obtained by the signal processor 40. Alternatively, a stationary sample may be provided in the sample chamber 20.

The method proceeds to step 120 in which the signal processor generates an initial predictive analyte concentration model for the sensor by deriving the calibration coefficients $m(t_1, T_1)$ and $c(t_1, T_1)$ respectively based on the known analyte concentration $X_1$ as explained in more detail above. In step 130 it is checked if an initial drift model for the sensor is already available or required. If such an initial drift model is not yet available and indeed required, the method repeats steps 110 and 120 at $t=t_2$, to obtain $m(t_2, T_1)$ and $c(t_2, T_1)$. By determining $\Delta m(T_1)=m(t_2, T_1)-m(t_1, T_1)$ and $\Delta c=c(t_2, T_1)-c(t_1, T_1)$, a drift prediction model $D(T_1)$ for m and c may be derived. It is noted that if can be expected that such a drift is non-linear, steps 110 and 120 may be repeated a number of times at different points in time to allow for a non-linear regression to be performed on the set of calibration coefficients, as previously explained.

The method subsequently proceeds to step 140 where it is determined if the temperature-dependent drift prediction model has been generated. If this is not yet the case, steps 110 and 120 are repeated a number of times with a calibration fluid at a different set temperature as indicated by step 150 to obtain $m(t_i, T_2)$ and $c(t_i, T_2)$, wherein $t_i$ indicates a set of calibration measurements at different points in time and in which $T_2 \neq T_1$. The second cycle of calibration measurements may be performed with the same calibration fluid as used for the first cycle of calibration measurements or with a different calibration fluid having a concentration $X_2$ of the analyte of interest. In an embodiment, $X_1=X_2$. In an alternative embodiment, $X_1 \neq X_2$.

From this second cycle of calibration measurements, a second drift prediction model $D(T_2)$ may be derived in the same manner as $D(T_1)$, i.e. from $\Delta m(T_2)=m(t_2, T_2)-m(t_1, T_2)$ and $\Delta c=c(t_2, T_2)-c(t_1, T_2)$. Now, from $\Delta D(T_2-T_1)=D(T_2)-D(T_1)$, the temperature-dependent nature of the drift of the sensor $D(T)$ may be derived to obtain a calibration curve for the sensor including calibration coefficients $m(t,T)$ and $c(t,T)$, i.e. a calibration curve in which both m and c are defined as a function of both time and temperature.

Upon establishing this calibration curve in which the temperature-dependent drift model of the sensor is included, the method proceeds to step 160 in which the bodily fluid sample of a patient is being monitored. This may be achieved in any suitable manner, e.g. by flowing the sample through the sample chamber 20, or by providing the sample chamber 20 with a stationary sample.

In step 170 it is checked if recalibration is required. For instance, if the sensor produces a measurement result in step 160 that is unexpected or suspect, e.g. because the latest value of the analyte concentration calculated by the signal processor 140 suddenly significantly deviates from a pattern of earlier calculated analyte concentrations or lies outside a range of possible values, this may be an indication that the calibration curve is no longer valid such that the method may revert back to step 110 to initiate the process of obtaining a new calibration curve including a new temperature-dependent drift prediction model for the sensor as explained above.

Alternatively, a time period may be defined during which the sensor does not require recalibration, which time period starts from the completion of the most recent calibration of the sensor. In this embodiment, it is checked in step 170 if this time period has expired. If this is the case, the method revert backs to step 110 to initiate the process of obtaining a new calibration curve including a new temperature-dependent drift prediction model for the sensor as explained above.

In yet another alternative embodiment, which is shown in FIG. 6, step 170 comprises a periodic comparison 173 of the analyte concentration derived by the signal processor 40 from the sensor signal against an analyte concentration determined with a benchmark external analyzer in step 172. If it is found in step 174 that the difference between the analyte concentration derived by the signal processor 40 from the sensor signal and the analyte concentration determined with a benchmark external analyzer exceeds a defined tolerance, the method triggers the recalibration of the sensor in step 175, which causes the method of FIG. 5 to revert back to step 110 initiate the process of obtaining a new calibration curve including a new temperature-dependent drift prediction model for the sensor as explained above.

Upon returning to FIG. 1, if it is found in step 170 that no recalibration of the sensor is required, the method proceeds to step 180 in which it is checked if the monitoring of the patient needs to continue. If this is the case, the method reverts back to step 160. If not, the method is terminated.

In an embodiment, the calibration method of the present invention may be further refined by factoring in that upon exposure of a sensor at temperature $T_i$ to a calibration fluid having temperature $T_{a1}$, heat exchange between the sensor and the calibration fluid will mean that the equilibrium temperature of the sensor will be at $T_{a1}'$, which is a temperature in between temperatures $T_i$ and $T_{a1}$. Therefore, it will be necessary to compensate for this heat exchange as otherwise the calibration curve of the sensor as derived from the calibration measurements at different temperatures may be inaccurate due to the difference between assumed sensor temperature $T_{a1}$ and actual sensor temperature $T_{a1}'$.

A method for compensating for such heat exchange effects is shown in FIG. 7. The method starts by proceeding to step 210 in which a calibration fluid with a known concentration of the analyte is interest having a temperature $T_{a1}$ is passed over a sensor having temperature $T_i$. Temperature $T_i$ is typically different to $T_{a1}$, e.g. because of a previous calibration measurement at a different temperature or because of the sensor previously monitoring the concentration of the analyte of interest in a bodily fluid sample of a patient, e.g. a blood sample, urine sample, saliva sample, breath sample and so on. For instance, $T_{a1}$ may be room temperature (around 21° C.) and $T_i$ may be around the body temperature of the patient (e.g. around 37° C.). Consequently, the heat exchange between the sensor and the sample will cause the sensor to adopt temperature $T_{a1}'$ as previously explained.

Next, the analyte concentration in the sample is measured using the sensor at temperature $T_{a1}$ in step 220 as previously explained by generating sensor signal $V_{a1'}$. In a next step 230, the calibration solution is heated to $T_{a2}$ using the temperature control stage 25, and the analyte concentration in the sample is measured using the sensor at temperature $T_{a2}$ in step 240 as previously explained by generating sensor signal $V_{a2'}$. This measurement step may be preceded by stopping the flow of the calibration fluid over the sensors 21-23 as previously explained.

In step 250 it is checked if the correction for the heat exchange between the sensor and the calibration fluid has been completed. Such completion is achieved if the steps 210, 220, 230 and 240 have been performed at least twice. If not yet complete, the method returns to step 210 for a second set of measurements. In step 210, a second calibration fluid including the analyte of interest and having temperature $T_{a1}$ is passed over the sensor at temperature $T_{b2}$, which will bring the sensor to a temperature $T_{b1}$ by the heat exchange between the calibration fluid and the sensor, after which step 220 is repeated to obtain sensor signal $V_{b1}$. In step 230, the second calibration fluid and sensor are heated to $T_{b2}$ by the temperature control stage 25, after which in step 240 the sensor signal $V_{b1}$ is obtained. Temperature $T_{b1}$ should be as close as possible to $T_{a1}'$ to improve the accuracy of this correction method.

At this point, it is possible to calculate the sensor signal $V_{a1}$ for the first calibration fluid at $T_{a1}$ as follows:

$$V_{a1} = V_{a1'} + (V_{a2} - V_{a1'})\frac{(T_{b1} - T_{a1'})}{(T_{a2} - T_{a1'})} \qquad (3)$$

$V_{a1}$, $V_{a2}$, $V_{b1}$ and $V_{b2}$ can then be used to obtain the temperature-dependent drift model as previously explained with the aid of FIG. 5.

To carry out the calibration correction as described with the aid of FIG. 7 it is preferable to automate the control of the temperature control stage 25, detection of entry of calibration solutions and sensor measurement using the signal processor 40. In reality, heating and cooling of the sensor will occur at a finite rate. The sensor signal will then lag the temperature change by an amount that depends on the response time of the sensor. The analyte level of the calibration solution may not be stable over time, or with temperature changes. As a result, to minimise variability in the resulting calibration, it is preferable to make the calibration routine as consistent as possible, which include one or more of the following prerequisites:

There should be a fixed delay between the entry of the calibration solution and the temperature control stage 25 being activated. This delay should be no longer than is required to make a suitable measurement. Entry of the calibration fluid can be detected either by a change in temperature, and/or by a change in analyte level, as required.

The point at which to take a measurement can be based either on the temperature profile resulting from passing the calibration fluid over the sensor, or based on a fixed delay from the detection of the calibration solution, or an assessment of the change in sensor signal with time.

As soon as the measured temperature has been at the target temperature $T_{a2}$ or $T_{b2}$ for the minimum required time, a measurement should be made.

The point at which to take a measurement can be based on a fixed delay after reaching the target temperature, or on an assessment of the change in sensor signal with time.

In case of an unstable analyte of interest, it is desirable to minimise the time that elapses between heating the calibration fluid and obtaining the sensor measurement. One way of achieving this is to use the temperature control stage 25 to achieve the desired temperature, then flow the minimum required calibration solution over the sensor, such that the sensor returns to the appropriate temperature as rapidly as possible, i.e. the amount of heat exchanged between the sensor and fluid is minimized.

It is noted that ideally the selected calibration temperatures should span the operational range of the sensor. However, this may not be practical. Where the lowest operational temperature of the sensor is significantly below room temperature, the use of a chilled calibration solution for the lower temperature calibration may improve calibration accuracy. At the same time, the upper calibration temperature must be significantly above any allowed ambient temperature to ensure adequate temperature control. Where the analyte of interest becomes unstable as temperature is increased, it may be necessary to lower the upper calibration temperature, trading the accuracy of the sensor measurement at the upper temperature against the reduction in accuracy for temperatures outside the calibration range.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

What is claimed is:

1. A method of calibrating a sensor of a monitoring apparatus for monitoring an analyte concentration in a bodily fluid sample of a patient, the method comprising:
    performing a first calibration cycle by:
        measuring a first response of the sensor to exposure to a first calibration fluid having a first concentration of said analyte at a first temperature;
        measuring a second response of the sensor to exposure to a second calibration fluid having a second concentration of said analyte at a second temperature;
        determining a temperature dependence in the sensitivity of the sensor from the first and second response;
    performing a second calibration cycle by repeating the first calibration cycle after a time interval;
    deriving a temperature-dependent drift function for the sensor from a difference between the temperature dependence determined in the first calibration cycle and the temperature dependence determined in the second calibration cycle;
    generating a calibration curve including said temperature-dependent drift function for said sensor;
    measuring a further response of the sensor to exposure to a first portion of the bodily fluid sample at a measurement temperature, said bodily fluid sample comprising an unknown amount of said analyte;
    estimating the amount of said analyte in said sample from said further response using said calibration curve;
    exposing a reference apparatus to a second portion of the bodily fluid sample;
    determining the amount of analyte in said sample with said reference apparatus;
    comparing the estimated amount with the determined amount; and
    creating an updated calibration curve by repeating the steps of performing the first and second calibration cycles, deriving the temperature drift function and generating the calibration curve in case a difference between the estimated amount and the determined amount exceeds a defined threshold.

2. The method of claim 1, wherein the first concentration and the second concentration are the same.

3. The method of claim 2, wherein the first calibration fluid and the second calibration fluid are the same.

4. The method of claim 1, wherein the first calibration cycle further comprises:
    measuring a third response of the sensor to exposure to a third calibration fluid having a third concentration of said analyte at a third temperature; and
    wherein the step of determining a temperature dependence in the sensitivity of the sensor comprises determining said sensitivity from the first, second and third responses.

5. The method of claim 1, further comprising repeating the steps of performing the first and second calibration cycles, deriving the temperature drift function and generating the calibration curve after a predefined period of time.

6. The method of claim 1, further comprising:
    periodically exposing said sensor to another bodily fluid sample of the patient; and
    repeating the steps of performing the first and second calibration cycles, deriving the temperature drift function and generating the calibration curve upon an uncharacteristic change in the sensor response during said periodic exposure.

7. A computer program product comprising a computer-readable storage medium, said medium comprising computer program code for implementing the method of claim 1 when executed on a processor of an apparatus for monitoring an analyte concentration in the bodily fluid sample of a patient.

8. An apparatus for monitoring an analyte concentration in the bodily fluid sample of a patient, the apparatus comprising:
    a sample chamber for receiving said bodily fluid sample, said sample chamber comprising the sensor for determining said analyte concentration in said bodily fluid sample;
    a fluid line fluidly connected to the sample chamber for providing the sensor with a calibration fluid;
    a temperature control element for controlling the temperature of the calibration fluid in the sample chamber;
    the computer program product of claim 7; and
    a signal processor conductively coupled to the sensor, said signal processor being adapted to execute the computer program code of said computer program product.

9. The apparatus of claim 8, wherein the signal processor is adapted to control the temperature control element.

10. The apparatus of claim 8, wherein the temperature control element is placed in the sample chamber.

11. The apparatus of claim 8, wherein the apparatus further comprises a temperature sensor for monitoring the temperature in the sample chamber.

12. The apparatus of claim 8, wherein the apparatus is a cardiopulmonary bypass apparatus.

* * * * *